(12) United States Patent
Moore

(10) Patent No.: US 7,274,316 B2
(45) Date of Patent: Sep. 25, 2007

(54) SYSTEM AND METHOD FOR MANAGING DATA FROM A FLOW ANALYZER

(75) Inventor: Douglas E. Moore, Round Rock, TX (US)

(73) Assignee: Luminex Corporation, Austin, TX (US)

( * ) Notice: Subject to any disclaimer, the term of this patent is extended or adjusted under 35 U.S.C. 154(b) by 0 days.

(21) Appl. No.: 11/282,265

(22) Filed: Nov. 16, 2005

(65) Prior Publication Data
US 2006/0106978 A1 May 18, 2006

Related U.S. Application Data

(60) Provisional application No. 60/628,715, filed on Nov. 17, 2004.

(51) Int. Cl.
*H03M 1/00* (2006.01)

(52) U.S. Cl. ...................................... 341/124; 341/122

(58) Field of Classification Search ......... 341/120–170
See application file for complete search history.

(56) References Cited

U.S. PATENT DOCUMENTS

| 5,278,988 A * | 1/1994 | Dejean et al. ............. 455/2.01 |
| 5,550,058 A | 8/1996 | Corio et al. |
| 6,658,357 B2 | 12/2003 | Chandler |
| 6,809,804 B1 | 10/2004 | Yount et al. |

FOREIGN PATENT DOCUMENTS

GB 2317228 3/1998

OTHER PUBLICATIONS

International Search Report, PCT/US2005/041701, mailed Apr. 10, 2006.

* cited by examiner

*Primary Examiner*—Lam T. Mai
(74) *Attorney, Agent, or Firm*—Charles D. Huston; Mollie E. Lettang; Daffer McDaniel, LLP

(57) ABSTRACT

A system and method for processing sample data employing hardware, such as a Field Programmable Gate Array (FPGA), to process the sample data in small pipelined steps. The processing includes a circular buffer where the read and write of data is synchronous, preventing buffer overrun or data loss. This pipeline processing approach allows increasing data acquisition channels or additional processing steps without limiting processing speed.

16 Claims, 4 Drawing Sheets

| SAMPLE # | ADC DATA | SUM | SUM-BKG | PEAK |
|---|---|---|---|---|
| 1 | 669 | 5585 | 9 | 52 |
| 2 | 669 | 5505 | 0 | 52 |
| 3 | 661 | 5418 | 0 | 52 |
| 4 | 649 | 5351 | 0 | 52 |
| 5 | 649 | 5296 | 0 | 52 |
| 6 | 653 | 5255 | 0 | 52 |
| 7 | 672 | 5243 | 0 | 52 |
| 8 | 687 | 5273 | 0 | 52 |
| 9 | 717 | 5309 | 0 | 52 |
| 10 | 811 | 5357 | 0 | 52 |
| 11 | 1040 | 5499 | 0 | 52 |
| 12 | 1499 | 5878 | 81 | 52 |
| 13 | 2273 | 6728 | 527 | 81 |
| 14 | 3237 | 8352 | 1432 | 527 |
| 15 | 4079 | 10936 | 3097 | 1432 |
| 16 | 4536 | 14343 | 5693 | 3097 |
| 17 | 4492 | 18192 | 9070 | 5693 |
| 18 | 4048 | 21967 | 12883 | 9070 |
| 19 | 3371 | 25204 | 16610 | 12883 |
| 20 | 2623 | 27535 | 19705 | 16610 |
| 21 | 1926 | 28659 | 21657 | 19705 |
| 22 | 1379 | 28312 | 21931 | 21657 |
| 23 | 1001 | 26454 | 19960 | 21931 |
| 24 | 752 | 23376 | 15518 | 21931 |
| 25 | 596 | 19592 | 9033 | 21931 |
| 26 | 525 | 15696 | 1400 | 21931 |
| 27 | 514 | 12173 | 0 | 21931 |
| 28 | 538 | 9316 | 0 | 21931 |
| 29 | 583 | 7231 | 0 | 21931 |

FIG. 3

SYSTEM AND METHOD FOR MANAGING DATA FROM A FLOW ANALYZER

PRIORITY APPLICATION

This application claims priority to Ser. No. 60/628,715 entitled "System and Method for Managing Data from a Flow Analyzer" filed Nov. 17, 2004.

BACKGROUND OF THE INVENTION

1. Field of the Invention

The present invention relates generally to an apparatus for, and a method of, increasing the quantity of information obtained from flow analyzers or other data collection devices by storing data relating to, for example, particles, cells, and inter-event background noise from flow through an examination zone. In particular, the present invention relates to an apparatus for and a method of increasing the rate that florescence samples may be taken, without loss of data, by splitting the sample processing into pipelined steps and using a circular buffer, or similar buffer or temporary storage capability.

2. Description of the Related Art

Flow cytometry is conveniently used to quickly measure one or more optical parameters of the cells and/or particles that pass through a light beam that impinges on a narrow examination zone. Background information on flow cytometry is found, for example, in Shapiro's Practical Flow Cytometry, Third Edition (Alan R. Liss, Inc. 1995), incorporated herein by reference in its entirety.

In conventional flow cytometers, sample fluid containing sample cells and/or particles is introduced from a sample tube into or near the center of a faster flowing stream of sheath fluid, which draws the sample toward the center of the combined streams. This process, known a hydrodynamic focusing, allows the cells and/or particles to be delivered reproducibly to the center of the measuring point in the flow cell or other examination zone. Typically, the cells and/or particles are in suspension in the flow cell.

A continuous wave laser focuses a laser beam on the cells and/or particles as they pass through the examination zone by a flow of a stream of the suspension. When an object of interest in the flow stream is struck by the laser beam, certain signals result and is sensed by detectors. For example, these signals include forward light scatter intensity, which provides information concerning the size of individual cells and/or particles, and side light scatter intensity, which provides information regarding the relative size and refractive properties of individual cells and/or particles.

Other signals which may be sensed by detectors include fluorescence emissions from one or more fluorescent dyes and/or other fluorescent molecules, for example, tryptophan or other fluorescent amino acid(s) or other molecule(s) that is native to a protein or other peptide, or to another biomolecule or man-made molecule. Typically, when a plurality of different fluorescing molecules is employed in an analytical scheme, fluorescence emission peaks are selected to minimize or, ideally, eliminate spectral overlap between the respective fluorescence emission peaks.

For example, ideally, fluorescence emission peaks will differ by 50 μm, though lesser (or larger) spectral separation also can be accommodated and used to advantage, for example, 20, 30 or 40 μm, where the greater the spectral separation, the more powerful is the discrimination between the respective fluorescence emitters. In addition, quantum efficiency is considered in the choice of fluorescent molecules. In the case of use of a plurality of different fluorescent molecules, a separate detector is tuned to and used for the different wavelength of emission of each fluorescence emitter. The excitation wavelength for more than one fluorescent molecule can be the same, or different excitation wavelengths can be used to match the excitation spectrum of each different fluorescent molecule.

The optical signals that are generated by an analytical procedure are transmitted to an output meter(s) and/or data storage means. Signal processing, for example, by a Digital Signal Processor (DSP) or a Field Programmable Gate Array (FPGA) can be employed before and/or after intensity data on the measured optical signals are transmitted to the output meter(s) and/or data storage means.

In flow cytometry, an "event" occurs when a cell or particle passes through the beam of the laser or other light source. As the event progresses, the light measured from scattering and/or fluorescence emission increases as the cell or particle enters the beam, reaches a maximum at the center of the beam, and tapers to a nominal value as it leaves the beam.

State of the art flow cytometers commonly use one of two systems to measure events. One system uses peak detectors, including peak hold circuits, to sustain the maximum signal level obtained from an event, and to measure optical parameters relating to cells and/or particles passing through a laser beam. Once a peak detector has sensed and measured an event, the peak detectors are turned off to provide sufficient time for an analog-to-digital (A/D) converter to digitize that maximum value of the signal. During the time that the peak detectors are off, termed "dead time," any event occurring within the laser beam will go undetected.

The second system uses an integrator to measure the area under the peak collected for an event. With either system, when an event occurs within the cytometer's light beam during the dead time, the event will go undetected.

Normally, such lack of detection of an event does not constitute a significant problem because, for a large number of events, only a tiny number will be missed. However, applications which require the detection of rare, critical events, for example, identification of one special cell or particle in a thousand or a million, suffer from the possible non-detection of a rare event when current generation flow cytometers are used for detection and measurement. The higher the throughput, the greater is the probability that such a critical event will be missed per unit time period.

One solution to problems encountered in sorting samples in flow cytometry is provided by U.S. Pat. No. 5,550,058 to Corio, et al., incorporated herein by reference. Corio, et al. provides a means of flexibly controlling decisions on the sorting of events detected in a flow cytometer. Events are pre-qualified according to user selectable parameters to permit reduction of events missed during dead time. However, the Corio, et al. reference does not teach or suggest a means of reducing the probability of missing a dead time event to zero.

U.S. Pat. No. 6,658,357 (incorporated by reference) provides a solution to the "dead time" problem and the capture of rare events. However, it employs asynchronous processes to write sample data to and read data from a circular buffer. In turn, the rate at which florescence samples may be taken is limited by DSP capabilities and memory. For example, increasing the florescence sample rate can result in insufficient DSP bandwidth and buffer overrun, which might result in sample data loss, which as noted above, is undesirable.

Thus, it would be beneficial in the art of flow analyzers, including flow cytometers or other analyzing equipment, to have a means to process increased florescence samples without the probability of missing any event or increasing buffer size.

It is further desirable to efficiently and inexpensively provide a system and/or method of maximizing sample rates while reducing the probability of missing an event for such high sampling rates.

SUMMARY OF THE INVENTION

The problems outlined above are solved by the system and method in accordance with the present invention. Broadly, the system includes a synchronous process to write sample data to and read data from a circular buffer. Samples are synchronously clocked into and out of the circular buffers. Writing a sample into a circular buffer causes the oldest sample to be removed from the circular buffer and processed. Sample rate is thus not limited by the circular buffer size and hardware resources, e.g. FPGA, and it is possible to increase the number of channels. Because the circular data buffers fill and empty at the same rate there is no possibility of buffer overrun and lost data.

One preferred embodiment of the present invention provides a system and method of increasing the amount of data while reducing the chance of lost data in flow analyzers, flow cytometers, and other measurement devices using synchronous processes to write sample data to and read data from a circular buffer. Samples are synchronously clocked into and out of the circular buffers. Writing a sample into a circular buffer causes the oldest sample to be removed from the circular buffer and processed. It is the sampling that drives the processing keeping the write and read processes in synchronization. Dual port ram is used so there is no competition between the read and write processes. Because the write and read processes are synchronized, buffer overrun is not possible and the buffer size is determined by the data required for the specific process algorithm. Increasing the number of FADC channels (Filter, Amplify, Digitize, Convert) does not decrease the sample throughput since channels are processed in parallel. Increasing the number of samples in a process (e.g. a running sum) does not decrease throughput since the running sum is updated with each incoming sample in real time.

In one form, the data processing is split into small pipelined steps, e.g. where the pipeline processing performs the logic and arithmetic operations on the sample data. This pipeline processing of the sample data is performed by a Programmable Logic Device (PLD) such as an FPGA or ASIC at the analog-to-digital conversion (ADC) sample rate for as many channels as desired, provided the PLD has sufficient internal logic and external pins. This hardware approach permits a high sample rate limited only by the lesser of the ADC time or intrinsic propagation delay in reading the ADC. Additionally, while the number of channels is limited only by the PLD resources, adding channels does not limit speed of the instrument. Because the sample data processing is internal to the PLD, it is possible to add processing substeps to the pipeline with no effect on throughput. Finally, because sample data write and read are synchronous, the circular buffer fills and empties at the same rate with no possibility of buffer overrun or loss of data.

BRIEF DESCRIPTION OF THE DRAWINGS

Other objects and advantages of the invention will become apparent upon reading the following detailed description and upon reference to the accompanying drawings in which:

FIG. 3 is a table of sample values for the process of FIG. 1; and

DESCRIPTION OF THE PREFERRED EMBODIMENTS

Figure 1:
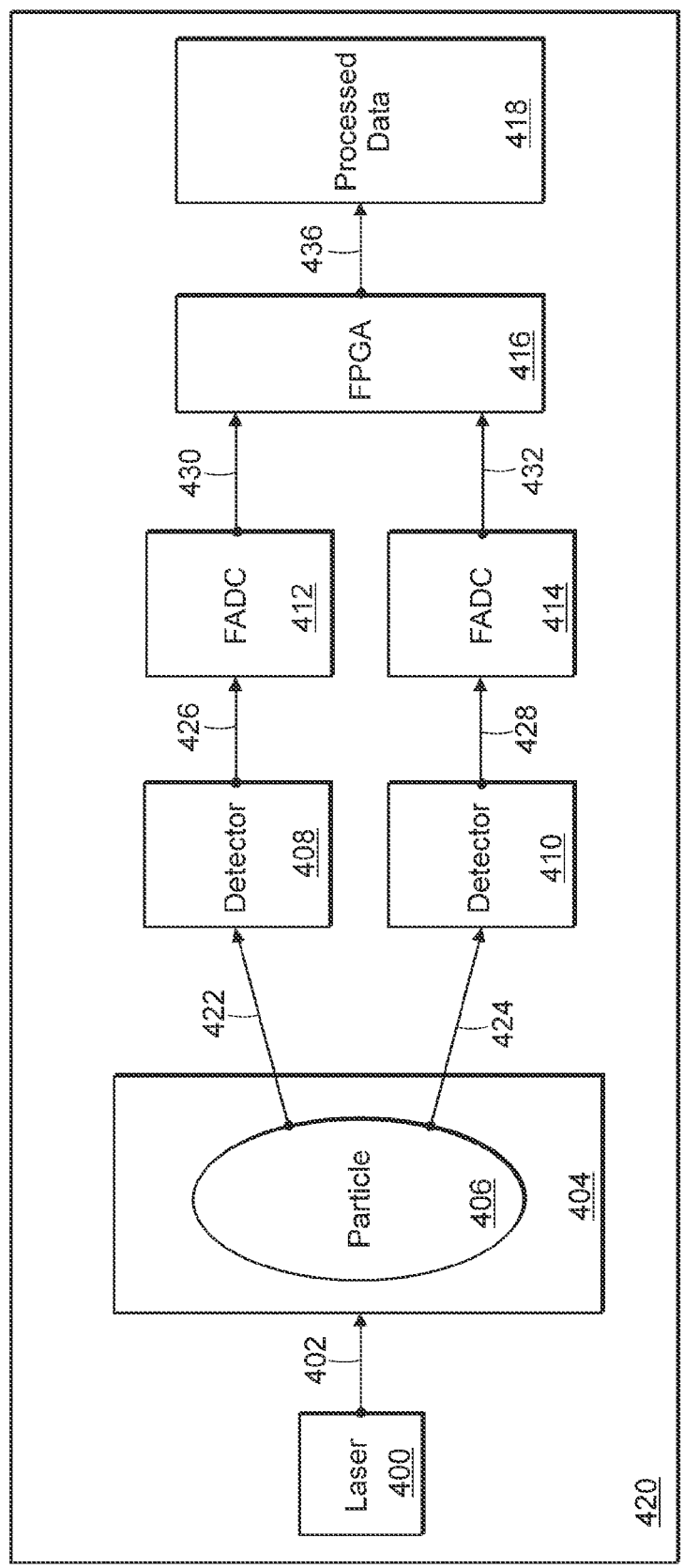
FIG. 1 is a schematic of a flow analyzer in accordance with the present invention.

Referring to FIG. 1, a schematic is shown for a functioning flow analyzer 420, for example, a flow cytometer. Laser light beam 402 from laser 400 is shown to impinge on a particle 406 as it passes through examination zone 404 of a flow cuvette. Light 422, 424 that is scattered, emitted (for example, fluorescence emission), refracted, or otherwise produced is then sensed by one or more detectors 408, 410, which then transmit their data 426, 428 to their respective FADC (filtering, amplification, and digital conversion) units 412, 414. The FADCs then transmit 430, 432 their respective resulting digitized data to a Programmed Logic Device (PLD) such as an FPGA, ASIC or other data processor 416 for final data processing. Such a PLD is a semiconductor device having logic components for performing logic and arithmetic operations with or without combinations with processors such as DSP's. Results of processing by the FPGA or other processor 416 are then output 436 as the final, processed data 418. While a processor such as a DSP can be used at 416, one advantage of the process of the present invention is to enable the use of a hardware logic solution, eliminating reading and storing sample data in internal DSP memory which uses a substantial portion of the DSP bandwidth, limiting the number of channels or processing time.

Figure 2:
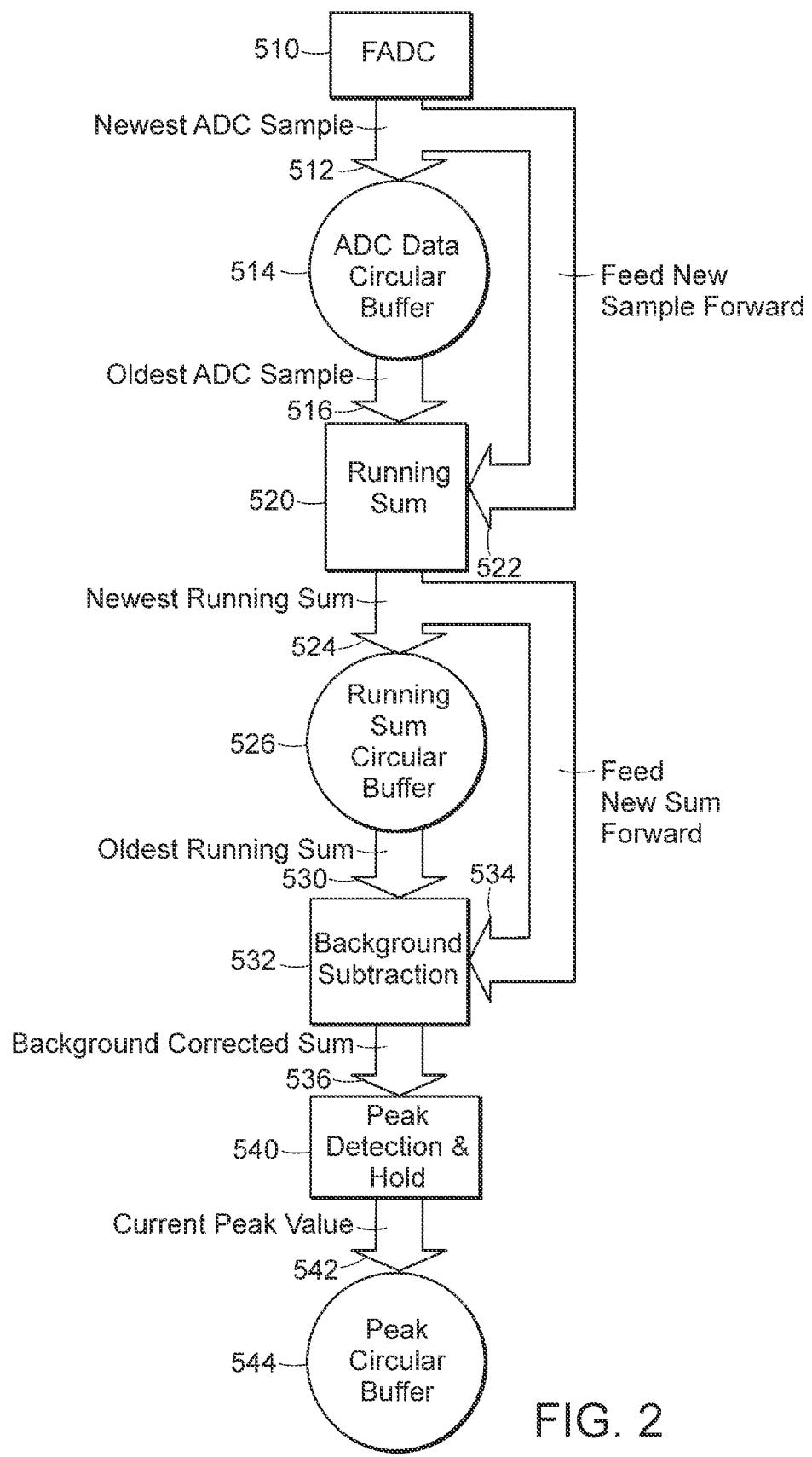
FIG. 2 is a flow diagram for an example process according to the instant invention.

Turning to FIG. 2, an exemplary pipeline process is illustrated. In FIG. 2, each function block may include a storage block and a processing block. One or more data elements are passed from the storage block to the processing block to be manipulated and output from the processing block. In the pipeline process of FIG. 2, the process receives florescence data, computes a running sum of the data; and subtracts background data from the running sum. Each pipeline process will preferably include one or more circular buffers, although it is understood such circular buffers may be multiple physical devices or a single data device divided into multiple buffers. It is important to recognize that other devices or methods can be used in place of circular buffers, and yet fulfill the accomplishments described herein. U.S. Pat. No. 6,658,357 describes "circular buffers" one of ordinary skill in the art would also understand that the circular buffer may constitute any memory configured for accepting a continuous stream of sample data and need not constitute physically contiguous memory (i.e. a "virtual" circular buffer) and memory might be dynamically allocated to constitute the circular buffer.

In more detail, FIG. 2 shows a sequence of function blocks arranged such that the output of one function block becomes the input of the next function block. Thus, in FIG. 2 the pipeline process receives florescence data from function block 510, computes a running sum of the data at 520, subtracts background data from the running sum at 532, while detecting peak running sums at 540.

The data storage blocks 514, 526, 544 in FIG. 2 are circular buffers composed of synchronous simple dual port ram having a data input bus, a data output bus, a read address bus, a write address bus, and an address counter. Each storage block 514, 526, 544 may have different depth and width as required by the processing to be performed. The dual port RAM is configured to output the old contents of the cell being written when the read and write address is the same, thus each new data value written to the circular buffer causes the oldest data value to be output from the circular buffer in a synchronous process.

Processing may but need not include saving a specified number of historical samples, computing and saving the running sum of a specified number of samples, subtracting a previous running sum from the newest running sum, and searching for the peak value of the background corrected running sum. The pipeline process of FIG. 2 is but a typical example; other processing steps may be added, subtracted, or modified as required.

While FIG. 1 illustrates a flow analyzer 420 having two data channels, an object of the present invention is to maximize the florescence data throughput, e.g. by increasing the number of channels or sample rate. Thus, the flow analyzer 420 would typically have multiple FADC channels processed in parallel, but FIGS. 2-4 is exemplary of data taken from a single channel for illustration.

Figure 4:
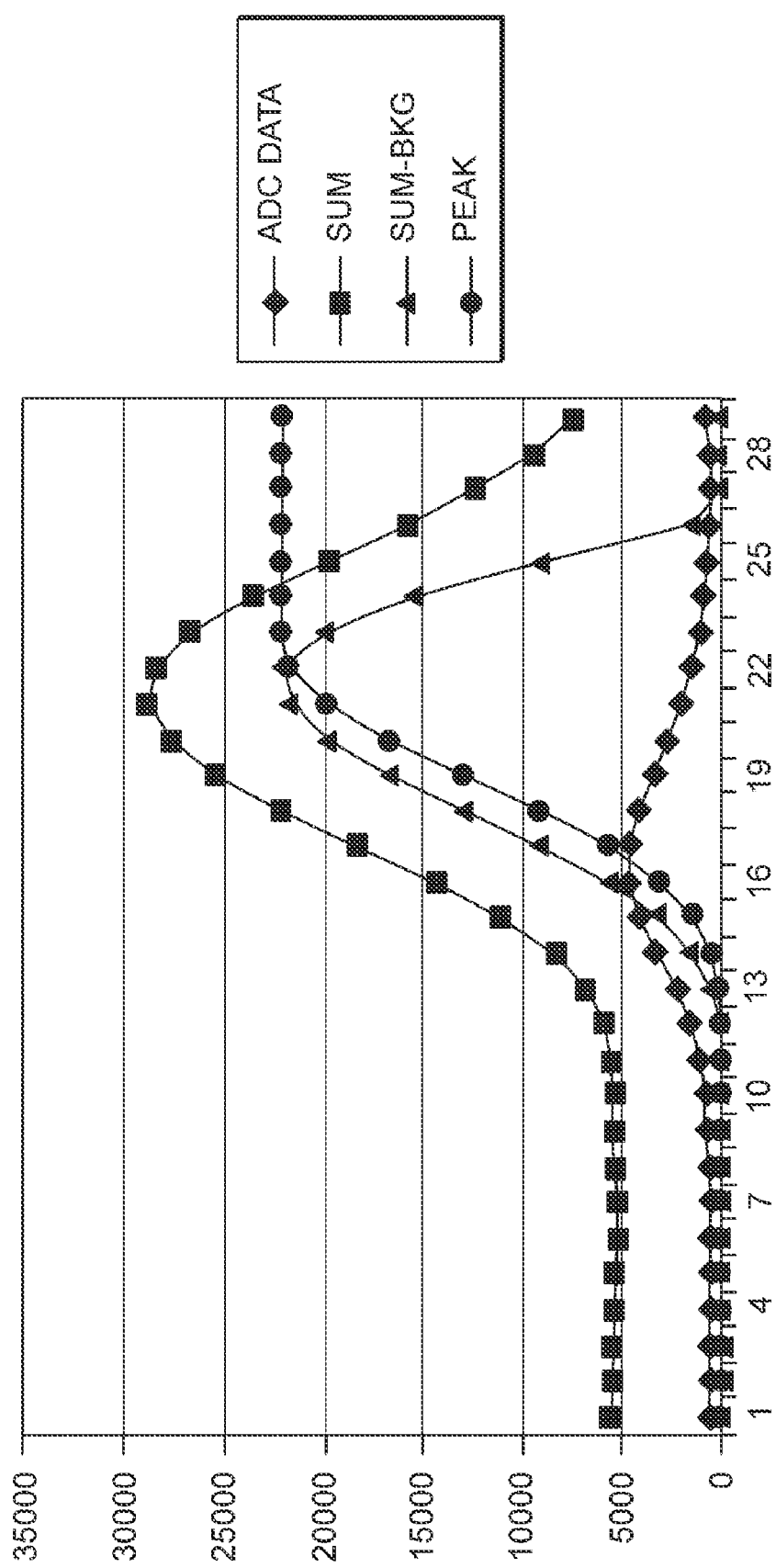
FIG. 4 is a graph plotting the sample values of the table of FIG. 2 for the process of FIG. 1.

FIGS. 3 and 4 show how samples are processed within the FIG. 2 pipeline. Each new incoming ADC DATA sample updates the pipeline by triggering an update to the ADC data, running sum, background corrected sum, and peak sum. As an example, assume circular buffer 514 contains the data shown in samples 12 through 19 of the column labeled ADC DATA, and 526 contain the values shown in samples 12 through 19 of the column labeled SUM. The following describes how the values in FIG. 3 sample 20 are computed. Looking at sample 19, running sum block 520 contains 25204, with inputs 3371 at 522 and 1040 at 516, producing a new sample 20 SUM value of 27535=25204+3371−1040 at 524. Background Subtraction block 532 has inputs of 25204 at 534 and 5499 at 530 producing a new sample 20 output SUM-BKG value of 19705=25204−5499 at 536. The peak detection and hold block 540 contains the previous peak value of 12883. The background corrected value of 16610 is present at 536, and being greater than 12883, will replace 12883 as the new PEAK sample 20 value. When the ADC conversion clocks the ADC DATA sample 20 value 2623 into circular buffer 514, it also clocks 27535 into circular buffer 526, 19705 into 532 and 16610 into 540.

It will be appreciated to those skilled in the art having the benefit of this disclosure that this invention is believed to provide systems and methods for managing data in a flow analyzer. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A method of collecting and processing data comprising the steps of:
    sampling a signal at a sample rate to collect sampled data, and storing the sampled data in a memory at the sample rate;
    reading the sampled data from said memory at approximately the sample rate to a Programmable Logic Device (PLD), wherein the storing, reading, and sampling of the sampled data are at approximately the same rate; and
    processing the sampled data with said PLD at about the sample rate, wherein said processing includes one or more processing substeps performing logic manipulation of said sampled data.

2. The method of claim 1, wherein the memory comprises a circular buffer.

3. The method of claim 1, wherein the processing step includes a plurality of substeps, each performing a logic manipulation of said sampled data.

4. The method of claim 3, wherein at least one of the substeps comprises an arithmetic operation.

5. The method of claim 1, wherein a plurality of signals are received by respective channels, and said sampling, reading, and processing steps are performed on each channel.

6. The method of claim 5, wherein said processing of sample data from each channel comprises a number of pipelined substeps.

7. The method of claim 1, wherein said PLD comprises a Field Programmable Gate Array (FPGA).

8. The method of claim 1, wherein said sampling occurs at an analog-to-digital conversion (ADC) rate, and said processing occurs at the lesser of said ADC rate or ADC sample propagation delay.

9. A particle flow analyzer comprising:
    a plurality of data channels, each sampling signals representative of particle flow phenomenon;
    a writer which accepts sampled data from each channel and writes it to a circular buffer;
    a reader which reads sampled data from a circular buffer substantially synchronously with the writer, wherein said write and reads to the circular buffer are at about the same rate; and
    a Programmable Logic Device (PLD) operable to process sampled data associated with a channel in one or more logic manipulation substeps.

10. The particle flow analyzer of claim 9, wherein said PLD comprises a Field Programmable Gate Array (FPGA).

11. The particle flow analyzer of claim 9, wherein said flow analyzer comprises a bead flow cytometer.

12. The particle flow analyzer of claim 9, wherein at least one circular buffer comprises memory space which is physically non-contiguous and dynamically allocated.

13. The particle flow analyzer of claim 9, wherein each channel comprises filter, amplify, digitize, and convert (FADC) channels.

14. A method of collecting and processing data in a flow analyzer, comprising the steps of:
    receiving incoming sampled data from a plurality of channels collected by said flow analyzer and using one or more circular buffers having a plurality of data storage areas;

storing incoming sampled data from respective channels in one or more respective circular buffers to direct the receipt and the storage of the sampled data collected by said flow analyzer into at least one of the plurality of data storage areas including overwriting of previously stored sampled data;

synchronously with storing, reading sampled data associated with a respective channel by at least one Programmable Logic Device (PLD) from at least one of the circular buffers; and processing the sampled data associated with a respective channel with said PLD without loss of the sampled data.

15. The method of claim 14, wherein said PLD comprises a Field Programmable Gate Array (FPGA).

16. The method of claim 14, wherein each channel has a PLD associated therewith, and said processing comprises a number of pipelined substeps performing logic on the associated sampled data.

* * * * *